(12) United States Patent
Santucci et al.

(10) Patent No.: US 8,833,139 B2
(45) Date of Patent: Sep. 16, 2014

(54) IMMERSION PROBE FOR ANALYSIS OF GASES IN MOLTEN METAL

(75) Inventors: Pablo Heigi Nakaoka Santucci, Sorocaba (BR); Artur Hess, Jr., Piedade (BR)

(73) Assignee: ECIL Met Tec Ltda., Piedade SP (BR)

( * ) Notice: Subject to any disclaimer, the term of this patent is extended or adjusted under 35 U.S.C. 154(b) by 0 days.

(21) Appl. No.: 13/585,530

(22) Filed: Aug. 14, 2012

(65) Prior Publication Data

US 2013/0042666 A1 Feb. 21, 2013

(30) Foreign Application Priority Data

Aug. 17, 2011 (BR) .................................. 1103889-6

(51) Int. Cl.
  *G01N 33/20* (2006.01)
  *G01N 1/22* (2006.01)
  *G01N 1/12* (2006.01)

(52) U.S. Cl.
  CPC .............. *G01N 33/203* (2013.01); *G01N 1/22* (2013.01); *G01N 2001/2288* (2013.01); *G01N 1/125* (2013.01)
  USPC ...................... 73/19.07; 73/863.31; 73/864.51

(58) Field of Classification Search
  CPC ............................ G01N 1/125; G01N 33/206
  USPC ................. 73/19.07, 863.31, 864.31, 864.53, 73/864.54, 864.55, 864.56, 864.57, 73/864.58, 864.59

See application file for complete search history.

(56) References Cited

U.S. PATENT DOCUMENTS

| | | | |
|---|---|---|---|
| 4,105,507 A | * | 8/1978 | VonKrusenstierna et al. .......................... 205/783.5 |
| 4,998,432 A | * | 3/1991 | Plessers et al. .............. 73/19.07 |
| 6,216,526 B1 | | 4/2001 | Junker et al. |
| 2008/0196476 A1 | * | 8/2008 | Gerits et al. ................. 73/19.07 |
| 2011/0271737 A1 | * | 11/2011 | Villarreal et al. ............ 73/19.07 |

FOREIGN PATENT DOCUMENTS

| | | | | |
|---|---|---|---|---|
| BR | 8806242 A | | 10/1989 | |
| JP | 63058153 A | * | 3/1988 | ............. G01N 27/58 |

* cited by examiner

*Primary Examiner* — Lisa Caputo
*Assistant Examiner* — Punam Roy
(74) *Attorney, Agent, or Firm* — Alston & Bird LLP

(57) ABSTRACT

An immersion probe for analysis of gases in molten metal is provided. The immersion probe generally comprises a gas sampler, a gas injection tube and a porous ceramic filter. The porous ceramic filter has a groove that associates it to the gas sampler, the groove comprising an outer portion and an inner portion with respect to the gas sampler, the inner portion of the porous ceramic filter having an increase in body for better association of the porous ceramic filter to the gas sampler. An adhesive material provides mechanical support of the porous ceramic filter, the adhesive material being located in both the inner portion and the outer portion of the gas sampler.

13 Claims, 2 Drawing Sheets

IMMERSION PROBE FOR ANALYSIS OF GASES IN MOLTEN METAL

CROSS-REFERENCE TO RELATED APPLICATIONS

This application claims priority to Brazilian Application No. PI1103889-6, filed Aug. 17, 2011, the contents of which are further hereby incorporated by reference.

BACKGROUND OF THE INVENTION

1. Technical Field

The present invention refers to an immersion probe for analysis of gases, which comprises a porous ceramic filter at its gas-collecting end.

2. Description of the Prior Art

Immersion probes for analysis of gases are now indispensable tools in the manufacture of metals, particularly important in the production of steel, wherein some specific gases are viewed as harmful elements. Because of this, it is necessary to monitor constantly the contents of these gases, as well as to adjust them at permitted levels. In this regard, the hydrogen content in molten steel in its liquid state is of extreme important, since certain non-permitted contents cause irreparable damages to the metal when the latter is in solid state.

Thus, the analysis of the amount of gases in molten metals is carried out by means of a disposable device called a probe, which is secured by a support and immersed into a bath of molten metal in a contained, which may be a metallurgical pot, furnace or another container whatever suitable for receiving molten metals. The probe has, at one of its ends, a porous ceramic filter that is associated to a gas sampling tube by addition of an adhesive material, usually cement or ceramic adhesive, which provides mechanical support for the porous ceramic filter in the gas sampling tube.

In this regard, in order to analyze the gas or the mixture of gases contained in the molten metal, a gas carrier known as high-purity Nitrogen is injected into the metal through an injection tube. The mixture of gases containing the high-purity Nitrogen is then extracted by suction through the immersion probe by means of the porous ceramic filter and sent subsequently to a meter through the gas-capturing tube, where the analysis of the mixture of gases takes place, preferably in a system with catharometer through heat conductivity of the gases.

Additionally, the operations of injecting the carrier gas into liquid steel an extraction of the mixture of gases contained therein are time-consuming operations and are carried out in an extremely aggressive environment due to, for instance, brutal thermal shocks, high temperatures, vibration, ferrostatic pressure, mechanical and chemical corrosion, among other factors. All these adversities require much from the immersion probe for gases, besides being dangers for the operator as well, and the stresses during the detection often reach limits that cause cracks and/or breaks in the porous ceramic filter, especially in the area of association between the gas sampling tube and the porous ceramic filter.

Thus, these cracks of the porous ceramic filter may be of various magnitudes, and there may even be total break thereof. Middle-size and large-size cracks may cause troubles during the detection and cause erratic readings of the value of gases contained in the steel. On the other hand, the break of the ceramic filter may allow the entry of liquid metal into the immersion probe and into the gas sampling tube, causing erratic measurements in the detection of gases, and so it is necessary to carry out a new detection operation by using a new probe, which prolongs the time of detecting gases, as well as increases the dangers for the operator.

In this regard, probes like those described are known from the prior art, as for example, the Brazilian patent PI 8806242, which describes and claims a probe, an apparatus and a method for the analysis of gases in molten metal. Another example of a probe for the analysis of gases in molten metal is also described in U.S. Pat. No. 6,216,526. This document describes a probe comprising a porous ceramic filter associated to a gas sampling tube, plus an adhesive material for mechanical support in this association, thus producing a sealing, but still with the same problems mentioned.

It should be noted that statistics demonstrate that errors in detecting the hydrogen contents may reach 20% of the read value, while the number of detection failures due to large cracks and/or break of the ceramic filter reaches 15%. The ideal value is 5% in both cases.

BRIEF SUMMARY

This invention has the objective of improving the existing immersion probes for detection of gases molten metal, so as to prevent penetration of molten metal in them, thus increasing the rate of success thereof and preventing possible erratic detections and increasing reliability in the value of the detections.

It is another objective of the present invention to reduce the detection times thereof and dangers to the operator, improving the quality of the probe, thus preventing the need for a larger number of operations to detect gases in molten metals by increasing the rates of success thereof.

A further objective of the invention is to reduce the amount of adhesive material required for mechanical support of the porous ceramic filter in the gas sampler.

In various embodiments, one describes an immersion probe for analysis of gases in molten metal, which comprises at least one gas sampler and a porous ceramic filter, and the gas sampler comprises an end portion associated to the porous ceramic filter. The gas sampler has also an inner portion and outer portion with respect to the end portion, the association between the end portion of the gas sampler and the porous ceramic tube being configured so that the ceramic material of the porous ceramic filter will surround the end portion of the gas sampler from its inner portion to the outer portion.

In this regard, the association is possible, since the porous ceramic filter comprises an increase in its body in the area of association with the gas sampler, this increase in its body being situated at the inner portion of the gas sampler after the association. Besides, the porous ceramic filter also comprises a groove which, in turn, has a front face comprising an inner end adjacent the inner portion and an outer end adjacent the end portion. In a various embodiments, both inner and outer ends have the same length taken from the back face of the porous ceramic filter to the opposite end of the groove that is associated to the end portion.

In this association, the groove of the ceramic filter has adhesive material for mechanical support of the gas sampler, the adhesive material being located in the association of the end portion with the groove, in both the inner and outer portions of the gas sampler. Additionally, in an exemplary description, the gas sampler has a cylindrical shape and comprises a concentric gas injection tube in its inner area, and both gas-sampler and gas-injection tubes are constituted by quartz.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

Figure 1:
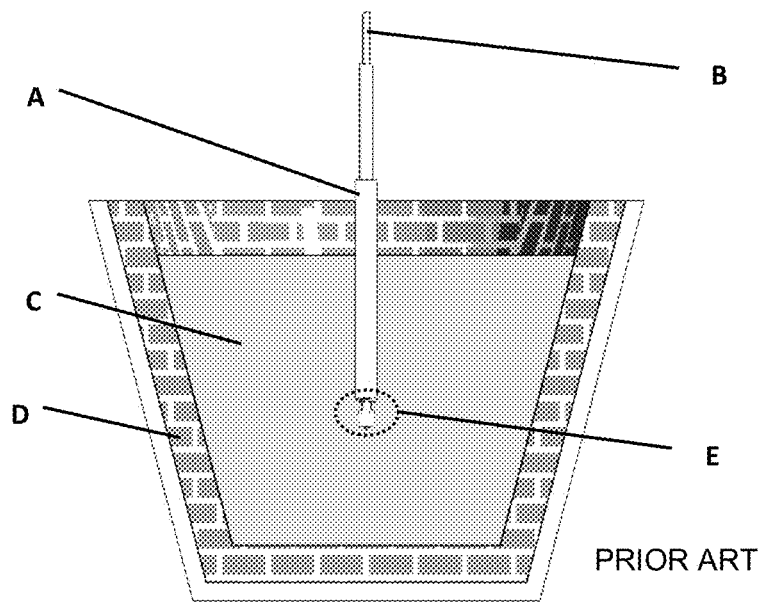
FIG. 1 is a sectional view of the prior art for gas detection in liquid metal.

In the prior art for detecting gas in molten metal, the analysis of the amount of gases is made by means of a disposable device, as shown in FIG. 1, which comprises an immersion probe A held by a support B, which is held by an operator during the analysis. A container D, which may be a metallurgical pot, furnace or another container whatever suitable for receiving molten metals, contains a molten metal C. The immersion probe A comprises an end E, which has a porous ceramic filter 1.

Figure 2:
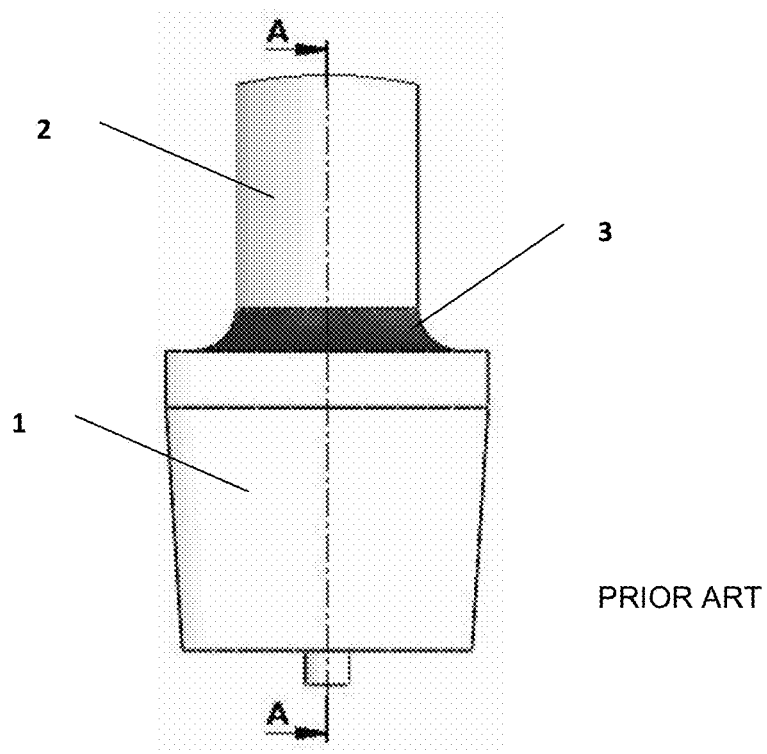
FIG. 2 is a detail view of the end E of FIG. 1.

The detail at the end E in FIG. 1 is represented in FIG. 2, which shows a gas sampler 2, which is associated to the porous filter 1 by means of an adhesive material 3. It should be noted that, in the prior art, this adhesive material 3 is located at the outer part of the gas sampler 2, as shown in FIG. 3, which represents this detail in sectional view in FIG. 2.

Figure 3:
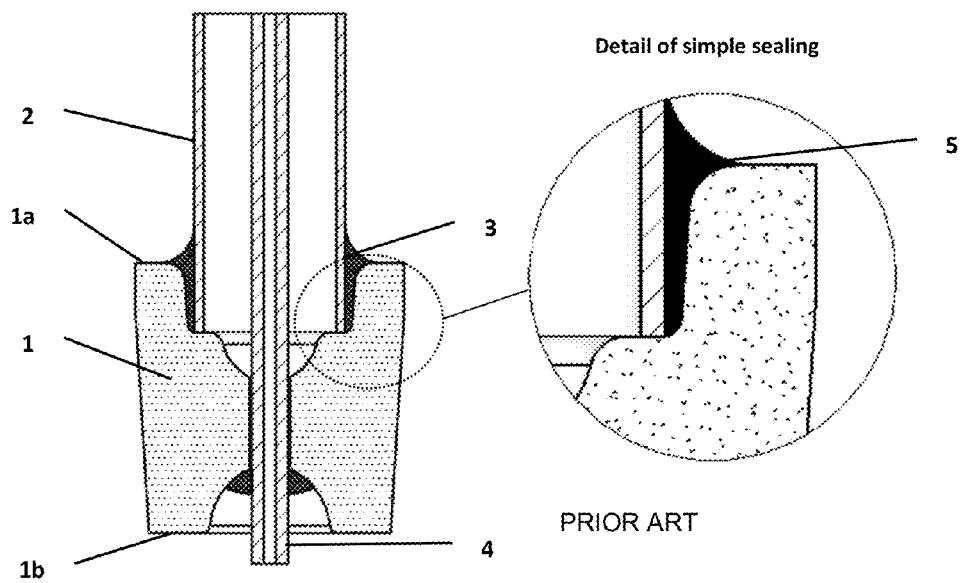
FIG. 3 is a sectional view of the prior art.

Further with regard to FIG. 3, one should be point out that the porous ceramic filter 1 comprises a back face 1b, which is the lower end of the immersion probe A, besides a front face 1a, which is opposed to the back face 1b and comprises a cavity for association of the gas sampler 2. The gas sampler 2 has a gas injection tube 4 inside it, which is used for injecting inert gas carrier and its sequent sampling for analysis. At the outer part of the gas sampler 2 an adhesive material 3 is added, which associates the porous ceramic filter 1 upon adhering to its cavity, as presented by detail 5. It should be noted that it is at this point that the association if weakest, and that is where most of the problems mentioned before occur.

Figure 4:
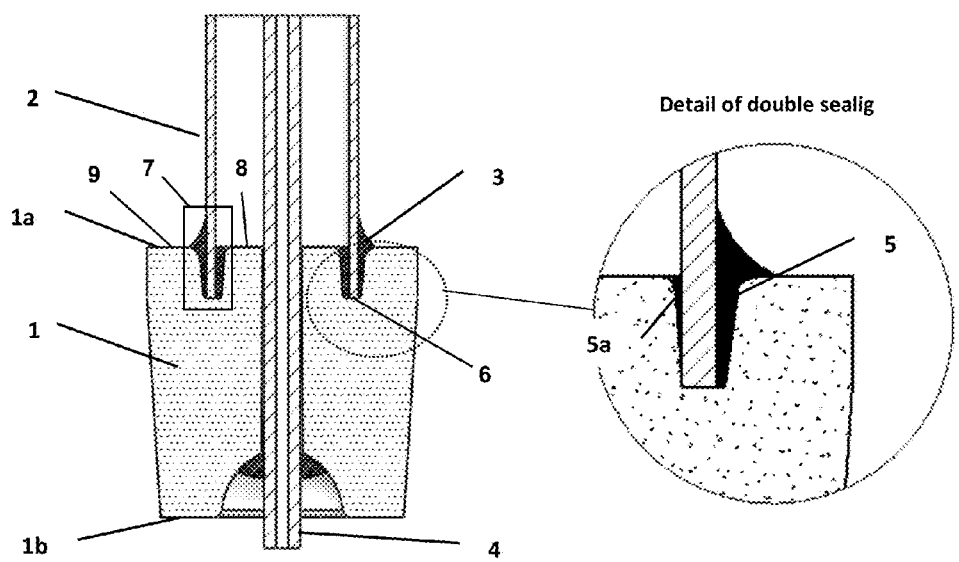
FIG. 4 is a sectional view of the present invention.

The present invention is illustrated in sectional view in FIG. 4, presents an immersion probe A for analysis of gases, which comprises a porous ceramic filter 1, which preferably has a specific shape with a protruding cylinder body at its central part. This porous ceramic filter 1 further has a back face 1b, which is the end of the immersion probe A for analysis of gasses, besides a front face 1a opposite the back face 1b.

In this regard, the front face 1a comprises a groove 7 that associates the porous ceramic filter 1 to a gas sampler 2, which is preferably cylindrical as well. The groove 7 comprises an increase in the body of the porous ceramic filter 1 protruding into the gas sampler 2, the latter being higher, with respect to the front face 1a, than the prior art, preferably between 6 and 10 mm, but with values ranging from 5 to 20 mm. It should be pointed out that, in the present invention, the gas sampler 2, which preferably has a concentric gas injection tube 4 inside it, is associated to the porous ceramic filter 1 in this groove 7 and, for this reason, the gas sampler 2 comprises an end portion 6 that separates the inner portion 8 from an outer portion 9.

Thus, the inner portions 8 and 9 form, preferably, planes parallel to the faces 1a and 1b, which define the relative heights of these portions. These relative heights between the planes of the inner portions 8 and 9 8 may be different or, preferably according to the invention, may have the same height for greater resistivity and better mechanical support of the porous ceramic filter 1. Besides, the mechanical support between the porous ceramic filter 1 and the gas sampler 2 is achieved by means of an adhesive material 3, which aids in providing better mechanical support to the assembly than the prior art because it is located at both the internal portion 8 and the external portion 9 of the groove 7.

Thus, in this configuration one forms a double sealing of the assembly between the porous ceramic filter 1 and the gas sampler 2, illustrated by the details 5 and 5a in FIG. 4, the sealing being considered double because the sealing is present both in the outer portion 9 and the inner portion 8 of the gas sampler 2. With this double sealing, in the case of a possible failure in the first sealing caused by a crack or break in this association of the porous ceramic filter 1 to the gas sampler 2, there is still the second sealing, which prevents the molten metal C from getting into the gas sampler 2, thus preventing error or failure in the detection of the immersion probe A for analysis of gases.

Another advantage of the configuration of the filter with double sealing is that the latter enables association of the porous ceramic filter 1 with the gas sampler 2 with a smaller amount of adhesive material 3. This adhesive material 3, usually a ceramic material or cement, is harmful to the immersion probe A, because both are hygroscopic and the water present therein implies less accurate detections. Therefore, the use of a smaller amount thereof may be considered one more advantage of the present invention.

An example of various embodiments having been described, one should understand that the scope of the present invention embraces other possible variations, being limited only by the contents of the accompanying claims, which include the possible equivalents.

That which is claimed:

1. An immersion probe for analysis of gases in molten metal, the immersion probe comprising:
    a gas sampler; and
    a porous ceramic filter,
    wherein:
        the gas sampler comprises an end portion that is associated to the porous ceramic filter, the gas sampler having an inner portion and an outer portion with respect to the end portion;
        the association between the end portion of the gas sampler and the porous ceramic filter is configured such that the ceramic material of the porous ceramic filter substantially surrounds the end portion of the gas sampler from its inner portion to its outer portion;
        the ceramic filter comprises a groove that has adhesive material for mechanical support of the gas sampler, located at the association of the end portion with the groove, in both the inner portion and the outer portion of the gas sampler;
        the adhesive material surrounds the end portion of the as sampler; and
        the adhesive material disposed in the inner portion of the as sampler is structurally different from the adhesive material disposed in the outer portion of the as sampler.

2. An immersion probe for analysis of gases in molten metal according to claim 1, wherein the porous ceramic filter comprises an increase in its body in the inner portion of the gas sampler.

3. An immersion probe for analysis of gases in molten metal according to claim 2, wherein the groove of the porous ceramic filter has a front face, which defines a plane parallel to a plane defined by the inner portion and to a plane defined by the outer portion.

4. An immersion probe for analysis of gases in molten metal according to claim 3, wherein the inner portion and the outer portion have the same height as the plane defined by the back portion of the porous ceramic filter.

5. An immersion probe for analysis of gases in molten metal according to claim 3, wherein the planes defined by the inner portion and the outer portion have different heights relative to a height of the plane defined by the back face of the porous ceramic filter.

6. An immersion probe for analysis of gases in molten metal according to claim 2, wherein the amount of adhesive material disposed in the inner portion is different from the amount of adhesive material disposed in the outer portion.

7. An immersion probe for analysis of gases in molten metal according to claim 6, wherein the adhesive material disposed in the inner portion of the gas sampler is flush with a surface of the ceramic filter.

8. An immersion probe for analysis of gases in molten metal according to claim 1, wherein the gas sampler has a cylindrical shape.

9. An immersion probe for analysis of gases in molten metal according to claim 1, wherein the gas sampler comprises a gas injection tube in its inner portion.

10. An immersion probe for analysis of gases in molten metal according to claim 9, wherein the gas injection tube has a cylindrical shape.

11. An immersion probe for analysis of gases in molten metal according to claim 9, wherein the gas sampler and the gas injection tube are concentric.

12. An immersion probe for analysis of gases in molten metal according to claim 9, wherein the gas injection tube is constituted by quartz.

13. An immersion probe for analysis of gases in molten metal according to claim 1, wherein the gas sampler is constituted by quartz.

\* \* \* \* \*

UNITED STATES PATENT AND TRADEMARK OFFICE
CERTIFICATE OF CORRECTION

| | | |
|---|---|---|
| PATENT NO. | : 8,833,139 B2 | |
| APPLICATION NO. | : 13/585530 | |
| DATED | : September 16, 2014 | |
| INVENTOR(S) | : Santucci et al. | |

It is certified that error appears in the above-identified patent and that said Letters Patent is hereby corrected as shown below:

In the Claims

Column 4

Line 56, "as" should read --gas--

Line 60, "as" should read --gas--

Signed and Sealed this
Thirteenth Day of January, 2015

Michelle K. Lee
*Deputy Director of the United States Patent and Trademark Office*